US008315962B1

(12) United States Patent  (10) Patent No.: US 8,315,962 B1
Horne  (45) Date of Patent: Nov. 20, 2012

(54) SYSTEM AND METHOD FOR MULTICLASS DISCRIMINATION OF NEURAL RESPONSE DATA

(75) Inventor: James Herbert Horne, Boulder, CO (US)

(73) Assignee: Science Applications International Corporation, San Diego, CA (US)

( * ) Notice: Subject to any disclaimer, the term of this patent is extended or adjusted under 35 U.S.C. 154(b) by 387 days.

(21) Appl. No.: 12/625,985

(22) Filed: Nov. 25, 2009

(51) Int. Cl.
*G06E 1/00* (2006.01)
*G06E 3/00* (2006.01)
*G06F 15/18* (2006.01)
*G06G 7/00* (2006.01)

(52) U.S. Cl. ........................................................ 706/22
(58) Field of Classification Search ................. 706/22
See application file for complete search history.

(56) References Cited

U.S. PATENT DOCUMENTS 5,701,398 A * 12/1997 Glier et al. ...................... 706/41

OTHER PUBLICATIONS

'fMRI brain computer intrfaces': Sitaram, IEEE signal magazine, Jan. 2008.*
'Locality and low dimensions in the prediction of natural experience from fMRI', Meyer, 2008, MIT press.*
'Elements of artificial neural networks': Mehrotra, MIT press, 1997, pp. 136-139.*
S. Perkins, et al., "Grafting: Fast, Incremental Feature Selection by Gradient Descent in Function Space," Journal of Machine Learning Research 3 (2003) pp. 1333-1356 published Mar. 2003.
Yizhao Ni, et al., "Kernel Methods for fMRI Pattern Prediction," pp. 296-697, 2008 IEEE.
T. Mitchell, et al., "Predicting Human Brain Activity Associated with the Meanings of Nouns," www.sciencemag.org, pp. 1191-1195, vol. 320, May 30, 2008.
F. Meyer, et al., "Locality and low-dimensions in the prediction of natural experience from fMRI," MIT Press. 2008, pp. 1-8.
S. Ghebreab, et al., "Predictive Modeling of fMRI Brain States Using Functional Canonical Correlation Analysis," Springer-Verlag Berling Heidelberg 2007, pp. 393-397.
E. Olivetti, et al., "Mixture Models for Cognitive Brain State Prediction," pp. 1-8, http://pbc.lrdc.pitt.edu/?q=2007-results.
Pittsburgh Brain Activity Interpretation Competition 2007, "Combining Ridge and/or Partial Least Squares Regression," pp. 1-9, http://pbc.lrdc.pitt.edu/?q=2007-results.
Pittsburgh Brain Activity Interpretation Competition 2007, "Prediction of Dynamic Experiences with Neural networks and fMRI," pp. 1-5, http://pbc.lrdc.pitt.edu/?q=2007-results.
Pittsburgh Brain Activity Interpretation Competition 2007, "Support Vector Regression and fMRI," pp. 1-2, http://pbc.lrdc.pitt.edu/?q=2007-results.
G. Valente, et al., "Predictions of PBAIC 2007 Ratings with Linear Relevance Vector Machine regression," 1 page, http://pbc.lrdc.pitt.edu/?q=2007-results.

* cited by examiner

*Primary Examiner* — Omar Fernandez Rivas
*Assistant Examiner* — Peter Coughlan
(74) *Attorney, Agent, or Firm* — King & Spalding LLP

(57) ABSTRACT

Systems and methods are described herein for analyzing neural response data that can be assigned to multiple classes. The systems and methods begin with a set of training data from which optimal weight factors are derived. The derived weight factors are used in a classifier which is then applied to test data from test subjects. The classifier filters out the effects of less relevant data in the test data and provides a result in the form of probabilities associated with classes for the test data.

20 Claims, 3 Drawing Sheets

SYSTEM AND METHOD FOR MULTICLASS DISCRIMINATION OF NEURAL RESPONSE DATA

BACKGROUND OF THE INVENTION

1. Field of the Invention

The present invention relates generally to the field of neural response and more particularly to techniques for analyzing measured neural response data.

2. Description of the Related Art

Research has been done in the past to collect neural response data from individuals presented with two choices. The neural response data is typically collected from the brain using electroencephalogram ("EEG") or functional magnetic resonance imaging ("fMRI") equipment that can generate tens or hundreds of thousands of data points for a test subject. The neural response data has been analyzed to attempt to draw a correlation between the neural response data and the two choices. The goal of this analysis is to determine which of the two choices the test subject is going to select by examining the neural response data. The correlation of the neural response data with one of the two choices is referred to as classification. For example, if the test subject is shown an apple and an orange, the neural response data is collected and classified to determine whether the test subject is going to choose the apple or the orange. Because the test subject from whom the neural response data is collected only has two choices, the mathematical analysis is referred to as binary classifier analysis or binary discrimination analysis. A mathematical model for binary discrimination is described in an article by S. Perkins, K. Lacker, and J. Theiler, titled "Grafting: Fast, incremental feature selection by gradient descent in function space," published in the Journal of Machine Learning Research, 3:1333-1356 (2003), which article is incorporated herein by reference.

When a test subject is presented with more than two choices, such as selecting a key on a keyboard, the neural response data and the analysis thereof is more complicated. Each collected data point is a vector in a high dimensional feature space. Most of the features associated with each data point are irrelevant to the separation of the data into classes and including the irrelevant data decreases the performance of the classifier. Techniques other than the one described in the Perkins article have been used to study the discrimination between more than two mental states, in other words, when the test subject has more than two choices. However, prior techniques for multiclass discrimination have had limited success due to the complexity of the neural response data.

Previous work has been done in the classification of data into multiple categories, such as can be found in J. Zhu and T. Hastie, Kernel Logistic Regression and the Import Vector Machine, in T. G. Dietterich, S. Becker, and Z. Ghahramani, editors, NIPS, pages 1081-1088, MIT Press, 2001. However, this previous work has primarily focused on the case where the desired set of features is known ahead of time, and not on the case where a large number of features are irrelevant. Irrelevant features seriously degrade the performance of these types of classifiers, including support vector machines. What is needed is an approach to creating classifiers where the optimal feature kernel is not known ahead of time.

Research has been performed on distinguishing more than two mental states in fMRI data. Most of this research has focused on using basic machine learning techniques, but the performance of these techniques has been limited, particularly where there are a large number of features associated with the data.

For example, the Pittsburgh Brain Activity Interpretation Competition 2007 (PBAIC 2007) was an academic competition to determine techniques to classify fMRI data into multiple brain states. The results of the competition can be found at http://pbc.lrdc.pitt.edu/?q=2007-results. A variety of techniques were used in this competition, however, none provided a solution that unified feature selection and weight determination.

Previous efforts into classifying neural response data using EEG data have concentrated on the binary problem. Research on distinguishing more than two mental states in EEG data has been more limited. Because of the difficulty of distinguishing states, little has been done when the number of classes is larger than two.

SUMMARY OF THE INVENTION

Summary of the Problem

There is a need for a method of analyzing neural response data associated with multiple choices or classes. In other words, a need exists for an improved method of analyzing multiclass neural response data so that the more relevant features associated with the data can be identified and used to best classify the data.

Summary of the Solution

The embodiments of the present invention facilitate the analysis of neural response data where one is attempting to discriminate between more than two mental states. The approach described in this application unifies the feature selection and weight determination. The unified approach described here generally provides superior performance when compared to the types of techniques used in PBAIC 2007.

In a first exemplary embodiment, a system for analyzing the multiclass neural response data is described. The system comprises: a computer, a training software module for analyzing training data and creating a classifier, and a classifier software module for applying the classifier to data from actual testing. The training software module uses a loss function to analyze a set of training data and identify a set of optimal weights that produce a minimum for the loss function. The classifier software module uses the optimal weights in a classifier that can calculate, for each data point in a set of new neural response data, the probability the data point is associated with a particular class.

In a second exemplary embodiment, a computer-implemented method for analyzing multiclass neural response data is described. The computer-implemented method comprises a training software module that analyzes training data using a loss function and identifies a set of optimal weights that produce a minimum for the loss function. The training software module creates a classifier using the optimal weights. A classifier software module applies the classifier to data from actual testing to produce probabilities associated with the multiple choices presented to the test subject.

In a third exemplary embodiment, a computer-readable storage medium for analyzing multiclass neural response data is described. The computer-readable storage medium comprises first program instructions that use a loss function to analyze training data and identify a set of optimal weights that produce a minimum for the loss function. The first program instructions create a classifier using the optimal weights.

Second program instructions apply the classifier to data from actual testing to produce probabilities associated with the multiple choices presented to the test subject.

These and other embodiments are described in the detailed description that follows and the associated drawings.

BRIEF DESCRIPTION OF THE FIGURES

The preferred embodiments of the present invention are illustrated by way of example and are not limited to the following figures.

DETAILED DESCRIPTION OF THE EXEMPLARY EMBODIMENTS

The invention is directed to systems and methods using software modules to analyze neural response data. Although the exemplary embodiments will be generally described in the context of software modules running in a stand-alone computing environment, those skilled in the art will recognize that the present invention also can be implemented in conjunction with other program modules in a variety of other types of computing environments. For example, in a distributed computing environment, program modules may be physically located in different local and remote memory storage devices. Execution of the program modules may occur locally in a stand-alone manner or remotely in a client/server manner. Examples of such distributed computing environments include local area networks of an office, enterprise-wide computer networks, and the global Internet.

The detailed description that follows is represented largely in terms of processes and symbolic representations of operations in a computing environment by conventional computer components, which can include database servers, application servers, mail servers, routers, security devices, firewalls, clients, workstations, memory storage devices, display devices and input devices. Each of these conventional distributed computing components is accessible via a communications network, such as a wide area network or local area network.

The invention comprises computer programs that embody the functions described herein and that are illustrated in the appended flow charts. However, it should be apparent that there could be many different ways of implementing the invention in computer programming, and the invention should not be construed as limited to any one set of computer program instructions. Further, a skilled programmer would be able to write such a computer program to implement an exemplary embodiment based on the flow charts and associated description in the application text. Therefore, disclosure of a particular set of program code instructions is not considered necessary for an adequate understanding of how to make and use the invention. The inventive functionality of the claimed computer program will be explained in more detail in the following description read in conjunction with the figures illustrating the program flow.

Figure 1:
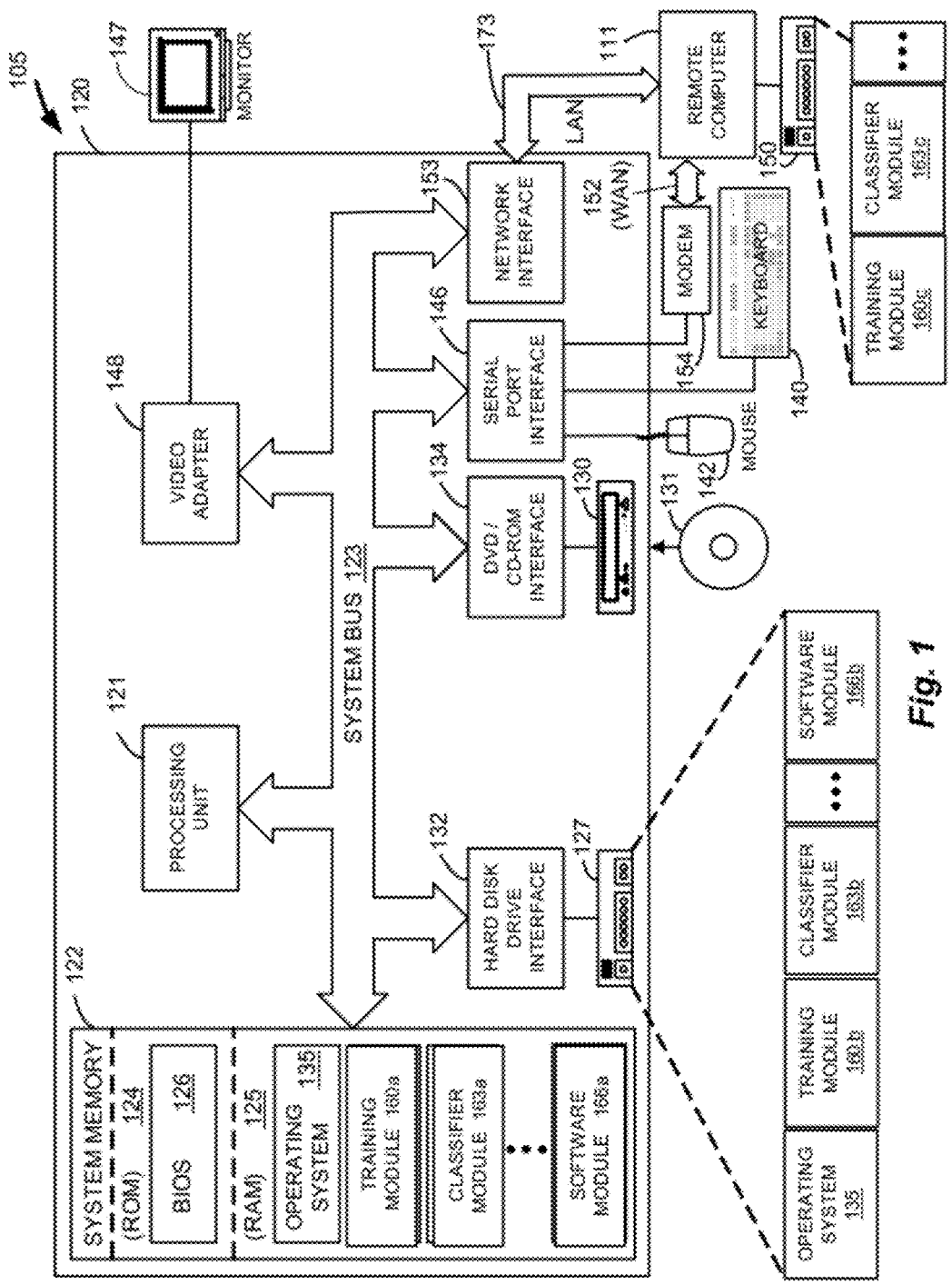
FIG. 1 illustrates components of a computer in accordance with an exemplary embodiment of the present invention.

Turning to the drawings, in which like numerals indicate like elements throughout the figures, exemplary embodiments of the invention are described in detail. Referring to FIG. 1, aspects of an exemplary computing environment are illustrated in which a system for analyzing neural response data operates. Those skilled in the art will appreciate that FIG. 1 and the associated discussion are intended to provide a brief, general description of the preferred computer hardware and software program modules, and that additional information is readily available in the appropriate programming manuals, user guides, and similar publications.

FIG. 1 illustrates a conventional computing device 120 suitable for supporting the operation of the preferred embodiment of the present invention. In FIG. 1, the computing device 120 operates in a networked environment with logical connections to one or more remote computers 111. The logical connections between computing device 120 and remote computer 111 are represented by a local area network 173 and a wide area network 152. Those of ordinary skill in the art will recognize that in this client/server configuration, the remote computer 111 may function as a file server or computer server. Those of ordinary skill in the art also will recognize that the invention can function in a stand-alone computing environment.

The computing device 120 includes a processing unit 121, such as "PENTIUM" microprocessors manufactured by Intel Corporation of Santa Clara, Calif. The computing device 120 also includes system memory 122, including read only memory (ROM) 124 and random access memory (RAM) 125, which is connected to the processor 121 by a system bus 123. The preferred computing device 120 utilizes a BIOS 126, which is stored in ROM 124. Those skilled in the art will recognize that the BIOS 126 is a set of basic routines that helps to transfer information between elements within the computing device 120. Those skilled in the art will also appreciate that the present invention may be implemented on computers having other architectures, such as computers that do not use a BIOS, and those that utilize other microprocessors.

Within the computing device 120, a local hard disk drive 127 is connected to the system bus 123 via a hard disk drive interface 132. A CD-ROM or DVD drive 130, which is used to read a CD-ROM or DVD disk 131, is connected to the system bus 123 via a CD-ROM or DVD interface 134. In other embodiments, other types of storage devices such as external hard disk drives and USB thumb drives can be used. A user enters commands and information into the computing device 120 by using input devices, such as a keyboard 140 and/or pointing device, such as a mouse 142, which are connected to the system bus 123 via a serial port interface 146. Other types of pointing devices (not shown in FIG. 1) include track pads, track balls, pens, head trackers, data gloves and other devices suitable for positioning a cursor on a computer monitor 147. The monitor 147 or other kind of display device is connected to the system bus 123 via a video adapter 148.

The remote computer 111 in this networked environment is connected to a remote memory storage device 150. This remote memory storage device 150 is typically a large capacity device such as a hard disk drive, CD-ROM or DVD drive, magneto-optical drive or the like. Those skilled in the art will understand that software modules are provided to the remote computer 111 via computer-readable media. The computing device 120 is connected to the remote computer by a network interface 153, which is used to communicate over the local area network 173.

In an alternative embodiment, the computing device 120 is also connected to the remote computer 111 by a modem 154, which is used to communicate over the wide area network 152, such as the Internet. The modem 154 is connected to the system bus 123 via the serial port interface 146. The modem 154 also can be connected to the public switched telephone network (PSTN) or community antenna television (CATV)

network. Although illustrated in FIG. 1 as external to the computing device 120, those of ordinary skill in the art can recognize that the modem 154 may also be internal to the computing device 120, thus communicating directly via the system bus 123. Connection to the remote computer 111 via both the local area network 173 and the wide area network 152 is not required, but merely illustrates alternative methods of providing a communication path between the computing device 120 and the remote computer 111.

Although other internal components of the computing device 120 are not shown, those of ordinary skill in the art will appreciate that such components and the interconnection between them are well known. Accordingly, additional details concerning the internal construction of the computing device 120 need not be disclosed in connection with the present invention.

Those skilled in the art will understand that program modules, such as an operating system 135 and other software modules 160a, 163a and 166a, and data are provided to the computing device 120 via computer-readable media. In the preferred computing device, the computer-readable media include local or remote memory storage devices, which may include the local hard disk drive 127, CD-ROM or DVD 131, RAM 125, ROM 124, and the remote memory storage device 150.

Figure 2:
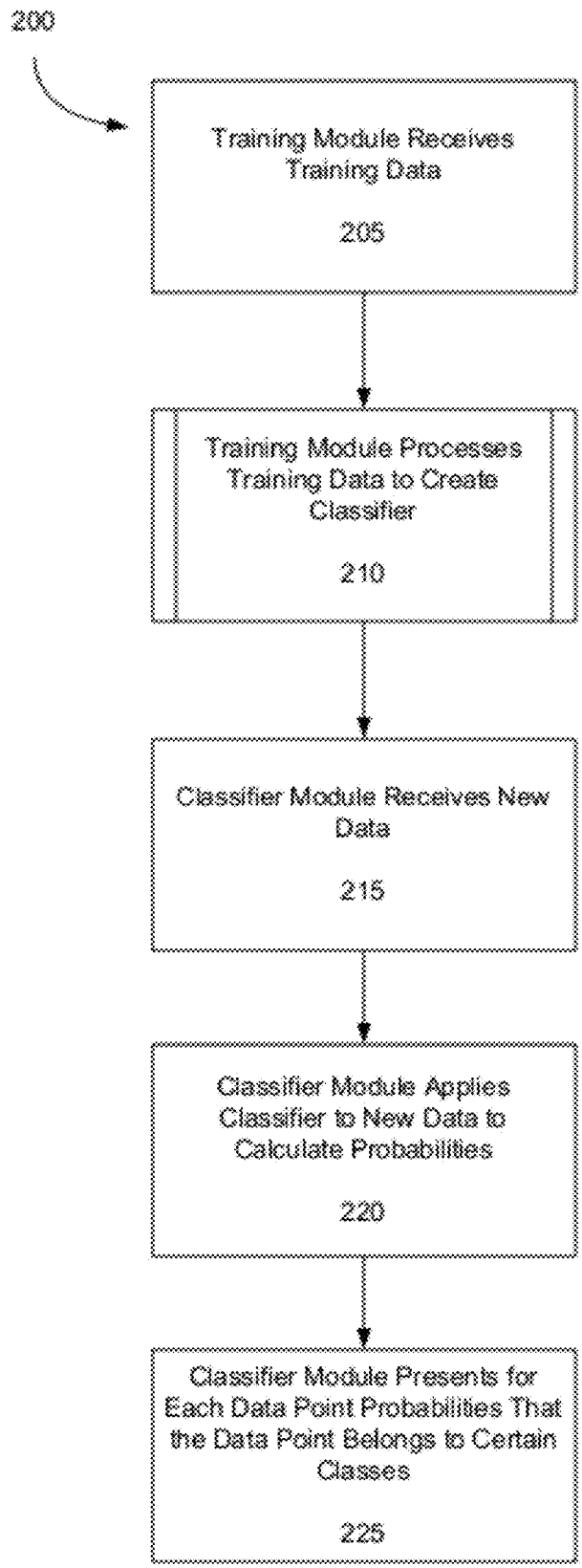
FIG. 2 illustrates a method for analyzing multiclass neural response data in accordance with an exemplary embodiment of the present invention.

Referring to FIG. 2, an exemplary method 200 for analyzing multiclass neural response data is illustrated. Turning now to step 205, the training module 160a receives and stores a set of training data. The training data are data collected where the test subject's choices were known. Using the example previously mentioned of a user making selections of keys on a keyboard, the training data would be data collected where it is known which keys the test subject is selecting. For example, certain data would be associated with the test subject selecting the key with letter "c" and other data would be associated with the test subject selecting the key with the number "6". The training module then uses the training data to determine which features in the data are most relevant to the test subject selecting the key with the letter "c" and which features in the data are most relevant to the test subject selecting the key with the number "6". Other less relevant features in the data can be minimized or ignored by using coefficients or weights in the calculations analyzing the neural response data. The methods and systems described herein are particularly helpful when the number of features is very large, but most of the features are not relevant. For example, for EEG and fMRI systems, the number of features can be in the tens or hundreds of thousands, but the best classification results generally can be obtained by using a small subset of less than a hundred features.

Once the training module 160a receives the training data, in step 210 the training module 160a will perform a series of calculations with the training data to create a classifier. The classifier includes weight factors for the more relevant features of the training data. The calculations the training module 160a performs to create the classifier are described in greater detail in FIG. 3 and the detailed description below associated with FIG. 3. Once the training module 160a creates the classifier with the appropriate weight factors, the classifier module 163a can use the classifier to analyze test data where it is not known which choices the test subjects made.

Referring to step 215, the classifier module 163a receives new test data where the test subject's selections are unknown. The classifier module's 163a job is to use the classifier to predict which selections the test subject made based on the new neural response data that was collected. In step 220, the classifier module 163a applies the classifier created by the training module 160a to the new neural response data. In applying the classifier to the new neural response data, the classifier module 163a calculates, for each data point in the new set of neural response data, a probability that the data point belongs to a particular class. In the example of selecting a key on a keyboard, each key is a class and the classifier module 163a determines the probability that a data point is associated with a key. Lastly, in step 225, the classifier module provides, for each data point, the probability that the data point belongs to a particular class. For example, the results from the classifier module 163a could indicate that a data point had an 80% probability of being associated with the "c" key, a 15% probability of being associated with the "t" key, and a 5% probability of being associated with the "d" key.

Those skilled in the art will appreciate that method 200 illustrated in FIG. 2 is merely exemplary. For instance, in alternate embodiments of the invention, the training module 160a and classifier module 163a performing the steps in FIG. 2 can be consolidated into a single software module or can be split up into multiple sub-component software modules.

The following is a more detailed example of how the training module 160a can create the classifier using the training data as referenced in step 210. The following methods allow for selection of the more relevant features from the high dimensional feature space of the collected training data. We begin with a set of training data that can belong to one of A classes, where A is greater than two. Each data point x in the training data is a vector of F features and these features can be either raw data or some projection into a high dimensional space. For EEG and fMRI data, it is often appropriate to perform PCA (principal component analysis) or ICA (independent component analysis) transforms on the data, and wavelets or windowed Fourier transforms can determine frequency responses. To give the regulated weights roughly equal weights, each feature should be scaled and normalized so that it has mean zero and variance one. The total number of data points is N.

The primary goal is to find a set of decision surfaces that classify new data points x. A training set is used to determine the parameters in the classifier. A regularized loss function is used that sets most of the features weights to zero. This approach is an extension of the grafting approach described in the Perkins article referenced above which only addressed the case of 2 classes.

The decision surfaces are hyperplanes defined by equation 1:

$$f_\alpha(x) = w_{\alpha 0} + \sum_{f=1}^{F} w_{\alpha f} x_f.$$

The weights $\omega_{\alpha f}$ are the key parameters to be determined in the training process. The probability that a data point x is of class $\alpha$ is given by equation 2:

$$p_\alpha(x) = \frac{e^{f\alpha(x)}}{\sum_{\beta=1}^{A} e^{f\beta(x)}}$$

The probabilities satisfy equation 3: $\Sigma_{\alpha=1}^{A} p\alpha(\chi)=1$. The goal is to determine the set of weights $\omega_{\alpha f}$ so as to give the best classification of the data points x.

Suppose we have a training set, and let $a_n$ be the class of the vector $x^{(n)}$. The most general regulated loss function is equation 4:

$$L_0 = -\sum_{n=1}^{N} c_{a_n} \log p_{a_n}(x^{(n)}) + \lambda_0 \#(w_{\alpha f} > 0) + \lambda_1 \sum_{\alpha=1}^{A} \sum_{f=1}^{F} |w_{\alpha f}| + \lambda_2 \sum_{\alpha=1}^{A} \sum_{f=0}^{F} w_{\alpha f}^2;$$

where $c_{an}$ is a normalization that is either $1/N$ or $1/N_\alpha$. The intent is that $\lambda_0$ is small enough to remove $\omega_{\alpha f}$ that are nearly zero, but not large enough to have much other impact. Similarly, $\lambda_2$ is non-zero only to break a symmetry. Otherwise, it will be treated as zero. Nearly all of the regularization and feature selection will be provided by $\lambda_1$.

The goal is to minimize $L_0$ by varying $\omega_{\alpha f}$. To simplify notation, we will prepend a zeroth feature $x_0 = 1$ to the feature vector when required. Notice that the $\lambda_1$ regularizing term does not include the zeroth feature, but the probabilities and the $\lambda_2$ regularizing term do. First, we calculate, with the following equation 5, that $$\frac{\partial \log p_\alpha(x)}{\partial w_{\beta f}} = x_f(\delta_{\alpha\beta} - p_\beta(x)).$$

The first derivative of $L_0$ with respect to $\omega_{\beta f}$ is (equation 6):

$$\frac{\partial L_0}{\partial w_{\beta f}} = -\sum_{n=1}^{N} c_{a_n} x_f^{(n)} (\delta_{a_n \beta} - p_\beta(x^{(n)})) + \lambda_1 \mathrm{sign}(w_{\beta f})(1 - \delta_{0f}) + 2\lambda_2 w_{\beta f}.$$

At the minimum, all of the derivatives in equation 6 should vanish. If we sum equation 6 over all possible classes β and set the result to zero, the first term vanishes because (equation 7):

$$\Sigma_\beta (\delta_{\alpha_n \beta} - p_\beta(\chi^{(n)})) = 1 - \Sigma p_\beta = 0.$$

The λ terms are then (equation 8):

$$0 = \lambda_1 \sum_{\beta=1}^{A} \mathrm{sign}(w_{\beta f})(1 - \delta_{0f}) + 2\lambda_2 \sum_{\beta=1}^{A} w_{\beta f}.$$

Consider these two terms separately. The $\lambda_1$ term says that the sum of the signs of feature weights are zero at the minimum. This means that for a given feature, there must be an even number of non-zero weights. In the preferred embodiment, all of the weights for a single feature are allowed to adjust.

The $\lambda_2$ term says that the sum of the weights for any feature equals zero at the minimum of $L_0$. The probabilities in equation 2 above are invariant under the shifts (equation 9):

$$\omega_{\alpha f} \to \omega_{\alpha f} + d^f \text{ for } f=0, \ldots, F.$$

This gauge freedom is fixed for all f by the $\lambda_2$ term. Thus, at the minimum of $L_0$ we should find (equation 10):

$$\sum_{\beta=1}^{A} w_{\beta f} = 0$$

for $f=0, \ldots, F$. Theoretically, we could impose this as a constraint by adding a Lagrange multiplier to the loss function in equation 4, but this can cause some numerical problems. In actual numerical experiments, the general solution in equation 8 holds approximately, but the constraint in equation 10 is not satisfied unless $\lambda_2$ is large. Instead, it can happen that all but one of the $\omega_{\beta f}$ are zero. However, the $\lambda_2$ term is still extremely useful as it breaks the gauge freedom, and removes a degenerate direction in the minimization.

Returning to $L_0$ with no constraints, the second derivative of $L_0$ is (equation 11):

$$\frac{\partial^2 L_0}{\partial w_{\beta f} \partial w_{\gamma g}} = \sum_{n=1}^{N} c_{a_n} x_f^{(n)} x_g^{(n)} p_\beta(x^{(n)})(\delta_{\beta\gamma} - p_\gamma(x^{(n)})) + 2\lambda_2 \delta_{\beta\gamma} \delta_{fg}.$$

In equation 11, when f=g, the second derivative is always non-negative as illustrated by the following explanation. For a single sample x, the probability part of the second derivative of $L_0$ is (equation 12):

$$P_{\beta\gamma} = p_\beta(\delta_{\beta\gamma} - p_\gamma).$$

Otherwise, the second derivative is the same as in the Perkins article referenced above. A unique global minimum will exist for $L_0$ if the determinant of the second derivative (equation 11) is positive. The $\lambda_2$ term in equation 11 makes a positive contribution to the second derivative that is proportional to the identity matrix, and only increases the determinant of equation 11. The probability part is a matrix of the form (equation 13):

$$P = \begin{pmatrix} p_1(1-p_1) & \ldots & -p_1 p_i & \ldots & -p_1 p_j & \ldots \\ \vdots & \ddots & \ldots & \ldots & \ldots & \ldots \\ -p_1 p_i & \ldots & p_i(1-p_i) & \ldots & -p_i p_j & \ldots \\ \vdots & \ddots & \ldots & \ldots & \ldots & \ldots \\ -p_1 p_j & \ldots & -p_i p_j & \ldots & p_j(1-p_j) & \ldots \\ \vdots & \ldots & \ldots & \ldots & \ldots & \ddots \end{pmatrix}.$$

In other words, the diagonal terms are $p_i(1-p_i)$ and the off-diagonal terms are $-p_i p_j$. The determinant of P is (equation 14):

$$\det P = \left(1 - \sum_{\alpha=1}^{A} p_\alpha\right) \prod_{\alpha=1}^{A} p_\alpha.$$

The Sylvester criterion says that P is a positive semi-definite matrix when the determinants of P and all of its principal minors are non-negative. The determinant in equation 14 is valid for any subset of the A probabilities. Since $0 \leq p_\alpha \leq 1$ and $\tau p_\alpha \leq 1$, with the equality when we sum over all A probabilities, the determinants in equation 14 are always non-negative. Thus P is a positive semi-definite matrix, and all of its eigenvalues are non-negative. Note that the first term for the full P is zero, so P has at least one null eigenvalue. The $\lambda_2$ term in equation 11 removes this null eigenvalue, and adds a positive number proportional to the identity matrix. Thus the determinant of the second derivative of $L_0$ is positive, and a unique global minimum exists.

In view of the foregoing, $L_0$ should have a unique minimum allowing use of a grafting approach. The exemplary process 210 for minimizing $L_0$ is set forth in the following description and illustrated in FIG. 3. In step 305, the training module 160a sets $\omega_{\alpha f}=0$ for all $\alpha$ and f. In step 310, the training module 160a allows $\omega_{\alpha 0}$ to vary for all $\alpha$ while keeping $\omega_{\alpha f}=0$ for f>0 and minimize $L_0$ in equation 4. In step 315 the training module 160a computes partial derivatives in equation 6. In step 320, the training module 160a finds feature $f_1$ that has the largest derivative, either for a specific class $\alpha$ or summed across all possible $\alpha$. In step 325, the training module 160a allows all of $\omega_{\alpha f1}$ to vary along with $\omega_0$ and minimizes $L_0$ again. Steps 305 through 325 are repeated again by the training module 160a in step 330 until all derivatives in equation 6 are less than $\lambda_i$. At that point, the positive second derivative in equation 11 ensures that allowing more features to vary will only increase $L_0$. In step 335, the training module 160a identifies the features and associated weights needed to minimize $L_0$. Lastly, in step 340, the training module 160a creates a classifier using the features and weights identified in step 335. The classifier the training module 160a creates from the training data can then be applied to new test data where the test subject's choices are unknown.

Figure 3:
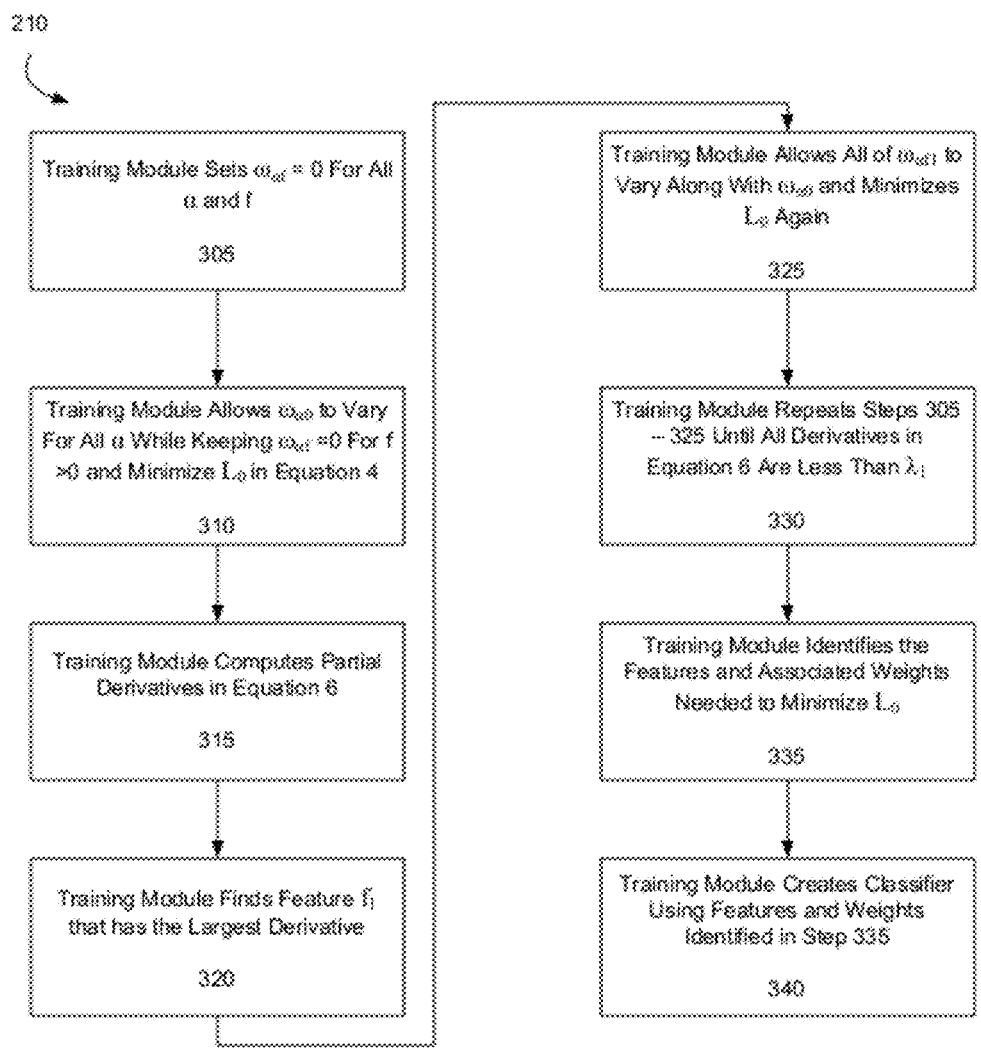
FIG. 3 illustrates in greater detail certain steps associated with the method of FIG. 2 in accordance with an exemplary embodiment of the present invention.

The following is a sample calculation using data to illustrate the steps of the exemplary methods illustrated in FIGS. 2 and 3.

TABLE 1

| Point x | Class $\alpha$ | $x_1$ | $x_2$ | $x_3$ | $x_4$ | $x_5$ | $x_6$ |
|---|---|---|---|---|---|---|---|
| 1 | 1 | 1.0145 | −0.5477 | −1.2846 | −1.6826 | −0.8166 | 0.4709 |
| 2 | 3 | −0.1244 | 0.1685 | 1.4722 | 0.0004 | 0.6305 | 0.3356 |
| 3 | 3 | −1.1733 | −1.0393 | 0.0646 | 0.2918 | 1.1358 | 1.2418 |
| 4 | 1 | 1.0187 | −0.1811 | −0.3967 | 0.9370 | −1.2477 | −0.9100 |
| 5 | 2 | −0.7355 | 1.5996 | 0.1445 | 0.4535 | 0.2980 | −1.1382 |

TABLE 2

| Class $\alpha$ | $w_{\alpha 0}$ | $w_{\alpha 1}$ | $w_{\alpha 2}$ | $w_{\alpha 3}$ | $w_{\alpha 4}$ | $w_{\alpha 5}$ | $w_{\alpha 6}$ |
|---|---|---|---|---|---|---|---|
| 1 | 0.2456 | 0.0723 | 0 | 0 | 0 | −1.5016 | 0 |
| 2 | −0.6105 | 0 | 1.4787 | 0 | 0 | 0 | 0 |
| 3 | 0.3649 | 0 | 0 | 0.6823 | 0 | 0 | 0.1287 |

TABLE 3

| Point x | $p_1(x)$ | $p_2(x)$ | $p_3(x)$ |
|---|---|---|---|
| 1 | 0.8422 | 0.0434 | 0.1144 |
| 2 | 0.0928 | 0.1316 | 0.7756 |
| 3 | 0.1018 | 0.0557 | 0.8425 |
| 4 | 0.8655 | 0.0401 | 0.0944 |
| 5 | 0.0977 | 0.7292 | 0.1731 |

Referencing Table 1 above, five different data points are used, each with six features. The features are normalized to mean zero and standard deviation one. Three separate classes (1, 2, or 3) are possible. The class and feature vectors for each point x are shown in Table 1.

To determine the fit, we use $c_{\alpha n}=1/N$ as referenced above in connection with equation 4, and set the regularizing terms to $\lambda_0=10^{-8}$, $\lambda_1=10^{-1}$, and $\lambda_2=10^{-7}$. For this example, $\lambda_0$ and $\lambda_2$ have been chosen to be small numbers. In the preferred embodiment, $\lambda_0$ and $\lambda_2$ will have magnitudes similar to those used in this example. In general, $\lambda_1$ should be chosen through N-fold cross-validation, a process that is known to those of skill in the art and described in the papers submitted at the PBAIC 2007 conference referenced above. N-fold cross-validation involves splitting a training set into N parts and training on all but one of the parts, while testing on the remaining part. The best $\lambda_1$ will give the best classification result when averaged across all N testing parts.

The results for the discriminant weights are shown in Table 2 above. The procedure starts by allowing all the weights $w_{\alpha 0}$ to vary, and minimizing the loss function in equation 4, while keeping $w_{\alpha i}=0$ for i>0. Then the derivative is taken (equation 6), the weight with the largest derivative is allowed to be non-zero, and the loss function (equation 4) is minimized again. The procedure terminates when the addition of further weights no longer decreases the loss function. In order, the grafting procedure finds $w_{15}$, $W_{22}$, $w_{33}$, $w_{36}$, and then $w_{11}$. The weights with non-zero values in Table 2 are the weights needed to minimize $L_0$ as referenced in step 335 above. All other weights are set to zero.

Finally, the classifier created using the weights from Table 2 is applied to the data to calculate the probabilities that each data point x belongs to a particular class. The probabilities that each point x belongs to a specific class are shown in Table 3. As the data in Table 3 shows, the highest probability for each point x is associated with the correct class identified in Table 1. With a smaller $\lambda_1$, the points would have been classified with higher probability into their correct classes, but at the expense of potentially overfitting the data.

In conclusion, the invention, as represented in the foregoing exemplary embodiments, provides systems and methods for analyzing a set of neural response data where each data point comprises multiple features. A training module can use a set of training data and a loss function to determine the optimal weights for minimizing the loss function and eliminating the insignificant features in the data. The optimal weights determined by the training module can be used in a classifier and applied to actual test data where the test subject's choices are not known. A classifier module applying the classifier to the actual test data can determine, for each data point in the set of actual test data, a probability associated with each potential choice for each data point.

The embodiments set forth herein are intended to be exemplary. From the description of the exemplary embodiments, equivalents of the elements shown herein and ways of constructing other embodiments of the invention will be apparent to practitioners of the art. For example, the methods for creating and applying a classifier may be modified but remain within the scope of the invention. Similarly, while representative software modules are described as performing the methods of the invention, variations of these software modules can also be used to execute the invention. Moreover, while the exemplary embodiments herein are described as applied to neural response data, the methods may also be applied to analyzing other types of data, such as computer vision, where the number of classes is large, and the potential number of features is very large. Many other modifications, features and embodiments of the invention will become evident to those of skill in the art. It should be appreciated, therefore, that many aspects of the invention were described above by way of example only and are not intended as required or essential elements of the invention unless explicitly stated otherwise. Accordingly, it should be understood that the foregoing relates only to certain embodiments of the invention and that numerous changes can be made therein without departing from the spirit and scope of the invention.

I claim:

1. A computer system for analyzing neural response data, the system comprising:

a processor, a computer-readable memory, and a computer-readable storage media;

the computer-readable storage media comprising a training module and a classifier module, wherein the training module uses a loss function to determine relevant features in a set of neural response training data, identifies a set of optimal weights that produce a minimum for the loss function according to an iterative procedure of setting at least one of the optimal weights to zero and identifying features based on partial derivatives of the loss function, and creates a classifier using the set of optimal weights;

the classifier module applies the classifier to a new set of neural response data and calculates, for a data point in the new set of neural response data, a probability that the data point is associated with a class, wherein the class represents an available choice for the neural response data; and the training module and the classifier module are stored on the computer-readable storage media for execution by the processor via the computer-readable memory.

2. The computer system of claim 1, wherein the new set of neural response data is collected by either EEG equipment or fMRI equipment.

3. The computer system of claim 1, wherein the set of optimal weights comprises at least a first weight, a second weight, and a third weight.

4. The computer system of claim 1, wherein the training module divides the set of neural response training data into a first subset of neural response training data and a second subset of neural response training data, uses the loss function to identify a first subset of optimal weights for the first subset of neural response training data, and identifies a second subset of optimal weights for the second subset of neural response training data.

5. The computer system of claim 4, wherein the training module compares the first subset of optimal weights and the second subset of optimal weights for verification.

6. The computer system of claim 1, wherein the class represents one of at least three available choices.

7. The computer system of claim 1, wherein the set of optimal weights include weights having a value of zero and weights having a value other than zero and the iterative procedure terminates when the addition of new weights to the set of optimal weights does not further minimize the loss function.

8. A computer-implemented method for analyzing neural response data comprising:
receiving a set of neural response training data;
determining, by a processor, relevant features of the neural response training data using a loss function, by identifying a set of optimal weights that produce a minimum for the loss function according to an iterative procedure of setting at least one of the optimal weights to zero and identifying features based on partial derivatives of the loss function;
creating a classifier using the set of optimal weights;
applying the classifier to a set of new neural response data; and
for a data point in the set of new neural response data, calculating a probability that the data point is associated with a class using the classifier, wherein the class represents an available choice for the neural response data.

9. The computer-implemented method of claim 8, wherein the set of new neural response data is collected by either EEG equipment or fMRI equipment.

10. The computer-implemented method of claim 8, wherein the set of optimal weights comprises at least a first weight, a second weight, and a third weight.

11. The computer-implemented method of claim 8, further comprising
dividing the neural response training data into a first subset of neural response training data and a second subset of neural response training data;
using the loss function to identify a first subset of optimal weights for the first subset of neural response training data; and
identifying a second subset of optimal weights for the second subset of neural response training data.

12. The computer-implemented method of claim 11, further comprising comparing the first subset of optimal weights and the second subset of optimal weights for verification.

13. The computer-implemented method of claim 8, wherein the class represents one of at least three available choices.

14. A computer-readable storage media storing computer readable instructions thereon that, when executed by a processor, direct the processor to perform a method for analyzing neural response data, the method comprising:
receiving a set of neural response training data;
determining, by the processor, relevant features of the neural response training data using a loss function by identifying a set of optimal weights that produce a minimum for the loss function according to an iterative procedure of setting at least one of the optimal weights to zero and identifying features based on partial derivatives of the loss function;
creating a classifier using the set of optimal weights;
applying the classifier to a new set of neural response data; and
for a data point in the new set of neural response data, calculating a probability that the data point is associated with a class using the classifier, wherein the class represents an available choice for the neural response data.

15. The computer-readable storage media of claim 14, wherein the new set of neural response data is collected by either EEG equipment or fMRI equipment.

16. The computer-readable storage media of claim 14, wherein the set of optimal weights comprises at least a first weight, a second weight, and a third weight.

17. The computer-readable storage media of claim 14, the method further comprising
dividing the set of neural response training data into a first subset of neural response training data and a second subset of neural response training data;
using the loss function to identify a first subset of optimal weights for the first subset of neural response training data; and
identifying a second subset of optimal weights for the second subset of neural response training data.

18. The computer-readable storage media of claim 17, the method further comprising comparing the first subset of optimal weights and the second subset of optimal weights for verification.

19. The computer-readable storage media of claim 14, wherein the class represents one of at least three available choices.

20. An apparatus for analyzing neural response data, the system comprising:
a computer-readable storage media; and
a processor configured to
determine relevant features of neural response training data using a loss function by identifying a set of optimal weights that produce a minimum for the loss function according to an iterative procedure of setting at least one of the optimal weights to zero and identifying features based on partial derivatives of the loss function, create a classifier using the set of optimal weights, apply the classifier to a set of new neural response data, and for a data point in the set of new neural response data, calculate a probability that the data point is associated with a class using the classifier, wherein the class represents an available choice for the neural response data.

* * * * *